(12) United States Patent
Cravens et al.

(10) Patent No.: US 7,801,269 B2
(45) Date of Patent: Sep. 21, 2010

(54) METHOD AND APPARATUS FOR CALIBRATING A RADIATION THERAPY TREATMENT SYSTEM

(75) Inventors: Robert L. Cravens, Verona, WI (US); Kenneth J. Ruchala, Madison, WI (US); Gustavo H. Olivera, Madison, WI (US); Daniel Lucas, Madison, WI (US); Andrea Cox, Fitchburg, WI (US); Paul J. Reckwerdt, Madison, WI (US); Cleber De Souza, Madison, WI (US); Douglas Henderson, Middleton, WI (US); David Arthur Spence, Hartland, WI (US)

(73) Assignee: TomoTherapy Incorporated, Madison, WI (US)

( * ) Notice: Subject to any disclaimer, the term of this patent is extended or adjusted under 35 U.S.C. 154(b) by 244 days.

(21) Appl. No.: 11/881,542

(22) Filed: Jul. 27, 2007

(65) Prior Publication Data

US 2008/0083871 A1    Apr. 10, 2008

Related U.S. Application Data

(60) Provisional application No. 60/820,690, filed on Jul. 28, 2006.

(51) Int. Cl.
*A61N 5/10* (2006.01)
*G01D 18/00* (2006.01)
(52) U.S. Cl. .......................... 378/65; 378/207
(58) Field of Classification Search .............. 378/4, 378/19, 62, 65, 145, 146, 147–150, 207; 250/252.1
See application file for complete search history.

(56) References Cited

U.S. PATENT DOCUMENTS

| | | | |
|---|---|---|---|
| 5,008,907 A | | 4/1991 | Norman et al. |
| 5,117,445 A | | 5/1992 | Seppi et al. |
| 5,394,452 A | * | 2/1995 | Swerdloff et al. ............. 378/65 |
| 5,692,507 A | | 12/1997 | Seppi et al. |

(Continued)

FOREIGN PATENT DOCUMENTS

JP    2000116643    4/2000

(Continued)

OTHER PUBLICATIONS

PCT/US2007/016920 International Search Report and Written Opinion dated Feb. 5, 2008, 10 pages.

(Continued)

*Primary Examiner*—Irakli Kiknadze
(74) *Attorney, Agent, or Firm*—Michael Best & Friedrich LLP (57) ABSTRACT

A radiation treatment system and method of commissioning the system, the system including a gantry, a radiation source operable to produce a beam of radiation, and a measurement device. The measurement device is physically connected to the gantry, and includes a multi-dimensional scanning arm, and a detector. The method includes generating radiation from the radiation source, passing the radiation through an attenuation block, and receiving radiation with the measurement device. The measurement device is positioned such that it is not in contact with water. Data is generated from the radiation received and the system is commissioned using the generated data to match system characteristics to a previously defined standard.

40 Claims, 12 Drawing Sheets

U.S. PATENT DOCUMENTS

| | | | |
|---|---|---|---|
| 5,748,703 A | 5/1998 | Cosman | |
| 6,322,249 B1 | 11/2001 | Wofford et al. | |
| 6,345,114 B1 * | 2/2002 | Mackie et al. | 382/132 |
| 6,438,202 B1 * | 8/2002 | Olivera et al. | 378/65 |
| 6,454,460 B1 | 9/2002 | Ramanathan et al. | |
| 6,466,644 B1 | 10/2002 | Hughes et al. | |
| 6,528,803 B1 | 3/2003 | Ritt | |
| 6,636,622 B2 | 10/2003 | Mackie et al. | |
| 6,675,116 B1 | 1/2004 | Ritt | |
| 6,760,402 B2 | 7/2004 | Ghelmansarai | |
| 6,810,107 B2 | 10/2004 | Steinberg | |
| 6,853,702 B2 | 2/2005 | Renner | |
| 6,904,125 B2 | 6/2005 | Van Dyk et al. | |
| 6,934,358 B2 | 8/2005 | Ritt et al. | |
| 6,934,653 B2 | 8/2005 | Ritt | |
| 6,937,751 B2 | 8/2005 | Ritt et al. | |
| 7,013,228 B2 | 3/2006 | Ritt | |
| 7,016,464 B2 | 3/2006 | Ritt et al. | |
| 7,024,026 B1 | 4/2006 | Ritt et al. | |
| 7,130,372 B2 | 10/2006 | Kusch et al. | |
| 7,233,688 B2 | 6/2007 | Ritt et al. | |
| 7,327,902 B2 | 2/2008 | Ritt et al. | |
| 7,639,851 B2 | 12/2009 | Ritt et al. | |
| 2003/0095625 A1 * | 5/2003 | Steinberg | 378/65 |
| 2004/0024300 A1 | 2/2004 | Graf | |
| 2005/0008121 A1 * | 1/2005 | Low et al. | 378/65 |
| 2005/0013406 A1 | 1/2005 | Dyk et al. | |
| 2006/0080057 A1 | 4/2006 | Ritt | |
| 2006/0159324 A1 | 7/2006 | Ritt et al. | |
| 2006/0215813 A1 | 9/2006 | Scherch et al. | |
| 2006/0219945 A1 | 10/2006 | Jaradat | |

FOREIGN PATENT DOCUMENTS

| | | |
|---|---|---|
| WO | 92/02277 | 2/1992 |
| WO | 02/24277 | 3/2002 |
| WO | 2004/105574 | 12/2004 |
| WO | 2005041835 | 5/2005 |

OTHER PUBLICATIONS

Extended European Search Report for European Application No. 07836301.7, Sep. 23, 2009.

Extended European Search Report for European Application No. 08005758.1, Sep. 23, 2009.

* cited by examiner

METHOD AND APPARATUS FOR CALIBRATING A RADIATION THERAPY TREATMENT SYSTEM

RELATED APPLICATIONS

This application claims priority to provisional patent application No. 60/820,690, filed Jul. 28, 2006, the entire contents of which are incorporated by reference herein.

FIELD OF THE INVENTION

This invention relates to a radiation therapy imaging and treatment system. More specifically, the invention relates to structure within the system that is utilized to calibrate the system, and to a method of commissioning or tuning the system.

BACKGROUND

Medical equipment for radiation therapy treats tumors tissue with high energy radiation. The dose and the placement of the dose must be accurately controlled to insure both that the tumor receives sufficient radiation to be destroyed, and that damage to the surrounding and adjacent non-tumorous tissue is minimized. Intensity modulated radiation therapy (IMRT) treats a patient with multiple rays of radiation each of which may be independently controlled in intensity and/or energy. The rays are directed from different angles about the patient and combine to provide a desired dose pattern. In external source radiation therapy, a radiation source external to the patient treats internal tumors. The external source is normally collimated to direct a beam only to the tumorous site. Typically, the radiation source consists of either high-energy X-rays, electrons from certain linear accelerators, or gamma rays from highly focused radioisotopes, though other types of radiation sources are possible.

Because the dose amount and dose placement need to be sufficiently controlled so as to ensure accurate patient treatment, the system itself needs to be commissioned properly at the outset and needs to be continuously monitored to ensure that the system is operating within the appropriate, and expected, parameters. When a system or machine is commissioned, the system characteristics are measured and compared against predetermined standards to configure the system and to ensure that the system is working within expected parameters. Commissioning includes consideration of total machine calibration, tuning the geometry of the beam delivered, and ensuring that the output and energy everywhere in the beam is equal, among other things. In some cases, individual systems are not calibrated with respect to each other, such that, in a way, each individual system stands alone in that variations in beam shape, strength, etc. can vary between machines. Each system is tuned to be within a manufacturing window, and a unique planning station model is generated. In effect, with each commissioning, you change the model to fit the machine.

SUMMARY

When commissioning is done in this manner, it is difficult to move a patient between individual systems once treatment has begun because of the necessary changes to dose and other treatment parameters that will need to be done to ensure that the patient is still receiving the appropriate treatment. Since the dose received by the patient depends not only on the beam shape and output but also varies with the energies within the beam itself, individual commissioning makes it difficult to move patients between machines once treatment has started. This type of individual commissioning also makes servicing and quality assurance (QA) analysis of the machines more difficult as there is no easy comparisons to make with known standards. Thus, it is desired to provide a treatment system that can be measured to a known set of standards for the purposes of commissioning, servicing, and QA analyses.

The present invention provides a radiation therapy treatment system that allows for easy calibration of the system with respect to a known set of standards, a.k.a. a "gold standard." The gold standard values can be determined in various ways, but are conventionally done using a water tank to produce the known attenuation results used to set the gold standard. By providing a radiation therapy treatment system capable of being tuned to the gold standard, the time and effort required to commission an individual system is reduced, and the system is easier to service and maintain from a QA standpoint. In effect, all systems are dosimetrically equivalent when tuned to the gold standard. Tuning machines to be dosimetrically equivalent is sometimes referred to as "twinning," and the resulting machines that are tuned to the gold standard are considered "twins." Because the tolerances of the systems stay the same from system to system, it is also possible to easily transfer patients from treatment on any individual system to another system without interfering with the patient's treatment plan. Tuning and commissioning becomes substantially automatic, and the machine can be changed to fit the model.

In one embodiment, the invention provides a radiation therapy treatment system. The system includes a radiation source operable to produce a beam of radiation, a gantry, and a measurement device coupled to the gantry. The measurement device includes a multi-dimensional scanning arm and a detector operable to receive radiation from the radiation source. In some embodiments, the system also includes an attenuation block coupled to a portion of the system, the attenuation block movable into and out of the path of the radiation beam produced by the radiation source. In one embodiment, the attenuation block comprises a plurality of aluminum plates coupled together to form a wedge that is substantially step-shaped. Radiation passed through the attenuation block is used to calibrate components of the system.

In another embodiment, the invention provides a method of commissioning a radiation therapy system to a previously defined standard. The radiation therapy system includes a measurement device coupled to a gantry, and a radiation source operable of producing radiation. The method includes the acts of generating radiation with the radiation source, passing the radiation through an attenuation block, receiving the radiation with the measurement device, generating data from the radiation received, and commissioning the system using the generated data to match system characteristics to the previously defined standard. The method also includes positioning the measurement device such that it is not in contact with water.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 1:
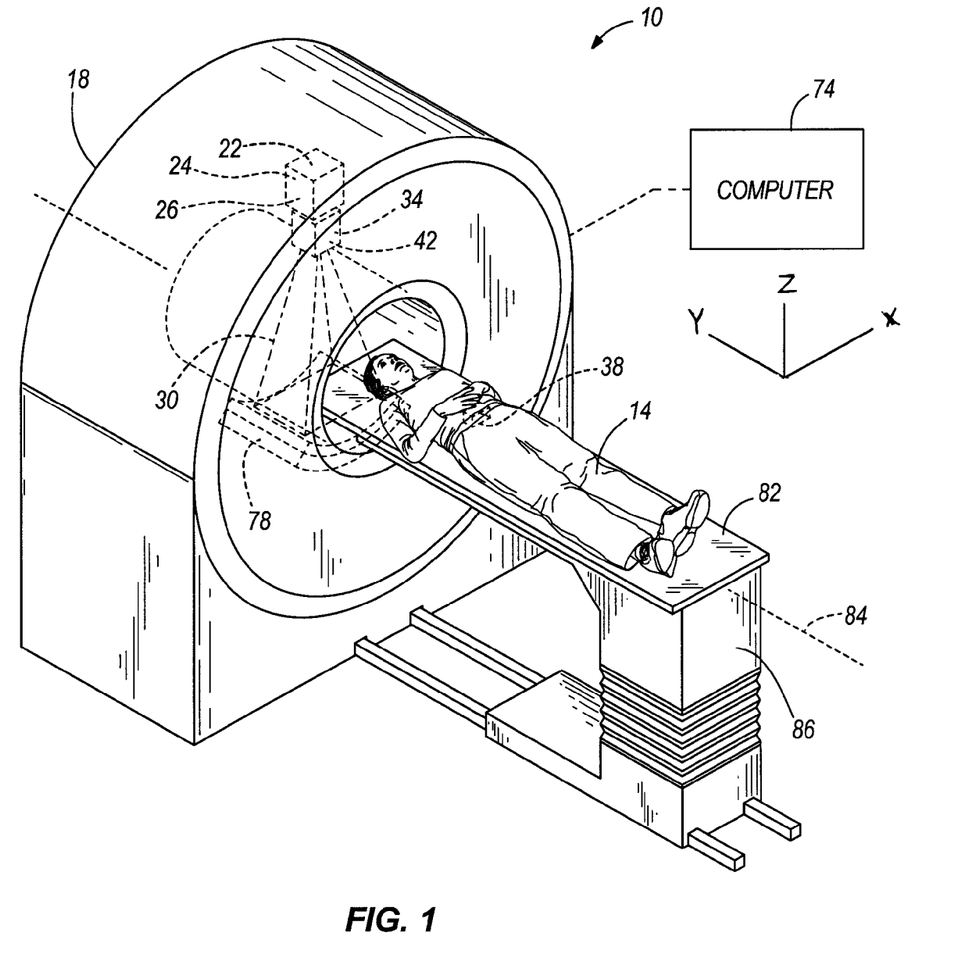
FIG. 1 is a perspective view of a radiation therapy treatment system.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 (a.k.a. "a linac") operable to generate a beam 30 of radiation. Though the gantry 18 shown in the drawings is a ring gantry, i.e., it extends through a full 360° arc to create a complete ring or circle, other types of mounting arrangements may also be employed. For example, a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped. The gantry 18 of the illustrated embodiment defines a gantry aperture 32 into which the patient 14 moves during treatment.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 30 is directed toward a portion 38 of the patient. Broadly speaking, the portion may include the entire body, but is generally smaller than the entire body and can be defined by a two-dimensional area and/or a three-dimensional volume. A portion or area desired to receive the radiation, which may be referred to as a target or target region, is an example of a region of interest. Another type of region of interest is a region at risk. If a portion includes a region at risk, the radiation beam is preferably diverted from the region at risk. Such modulation is sometimes referred to as intensity modulated radiation therapy ("IMRT").

Figure 2:
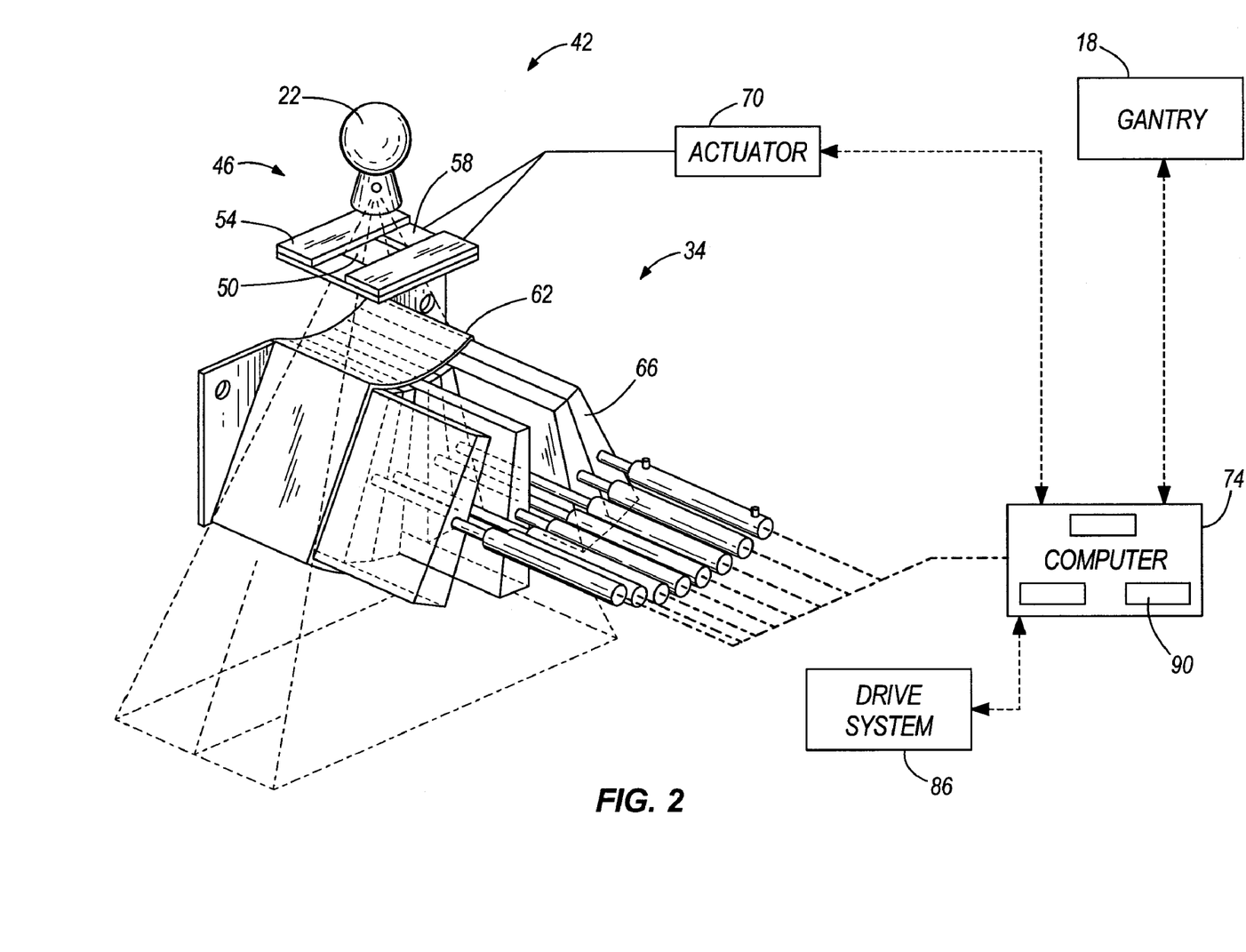
FIG. 2 is a perspective view of a multi-leaf collimator that can be used in the radiation therapy treatment system illustrated in FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50. The position of the jaws 46 regulates the shape of the beam 30 that is delivered to the patient 14.

In one embodiment, and illustrated in FIG. 2, the modulation device 34 can comprise a multi-leaf collimator 62 (a.k.a. "MLC"), which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the portion 38 on the patient 14. Each of the leaves 66 is independently controlled by an actuator 70, such as a motor or an air valve so that the leaf 66 can open and close quickly to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30, as illustrated in FIG. 1. The linear accelerator 26 and the detector 78 can also operate as a computed tomography (CT) system to generate CT images of the patient 14. The linear accelerator 26 emits the radiation beam 30 toward the portion 38 in the patient 14. The portion 38 absorbs some of the radiation. The detector 78 detects or measures the amount of radiation absorbed by the portion 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels. The system 10 can also include a patient support, shown as a couch 82, operable to support at least a portion of the patient 14 during treatment. While the illustrated couch 82 is designed to support the entire body of the patient 14, in other embodiments of the invention the patient support need not support the entire body, but rather can be designed to support only a portion of the patient 14 during treatment.

The first step in the twinning process introduced above is to set the gold standard against which all systems 10 will be measured. The gold standard is a standard of all the fundamental characteristics of the system that can be measured during commissioning, servicing, or the QA process (including calibration). The fundamental characteristics can include alignment, output, energy, beam shape, and the multi-leaf collimator 62. More specifically, transforming to the gold standard includes consideration of beam symmetry (linac alignment); intensity of source or number of photons released per second (output fluence rate); wavelength, color of light, or penetration depth of the radiation (energy); x and y-direction profiles, field width, and jaw position (beam shape); and leaf open/closed times and leaf response (MLC).

Figure 3:
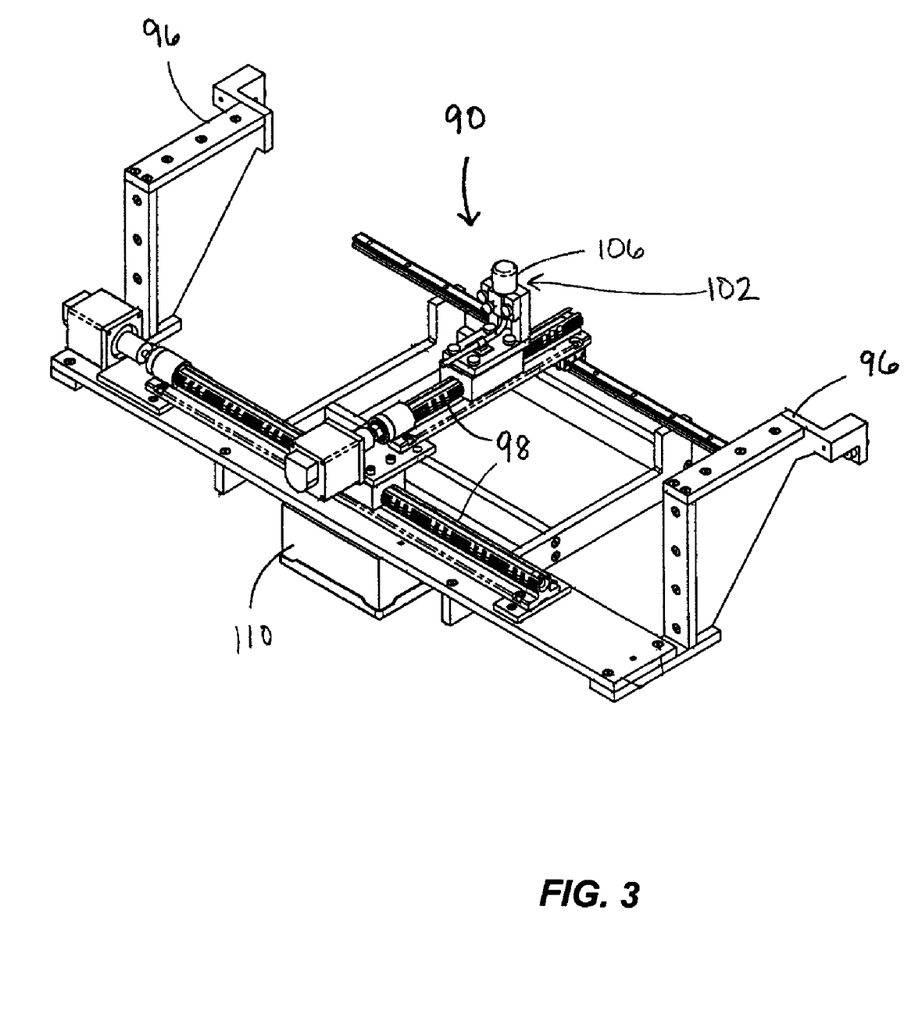
FIG. 3 is perspective view of a twinning arm for use in the radiation therapy system of FIG. 1.
Figure 4:
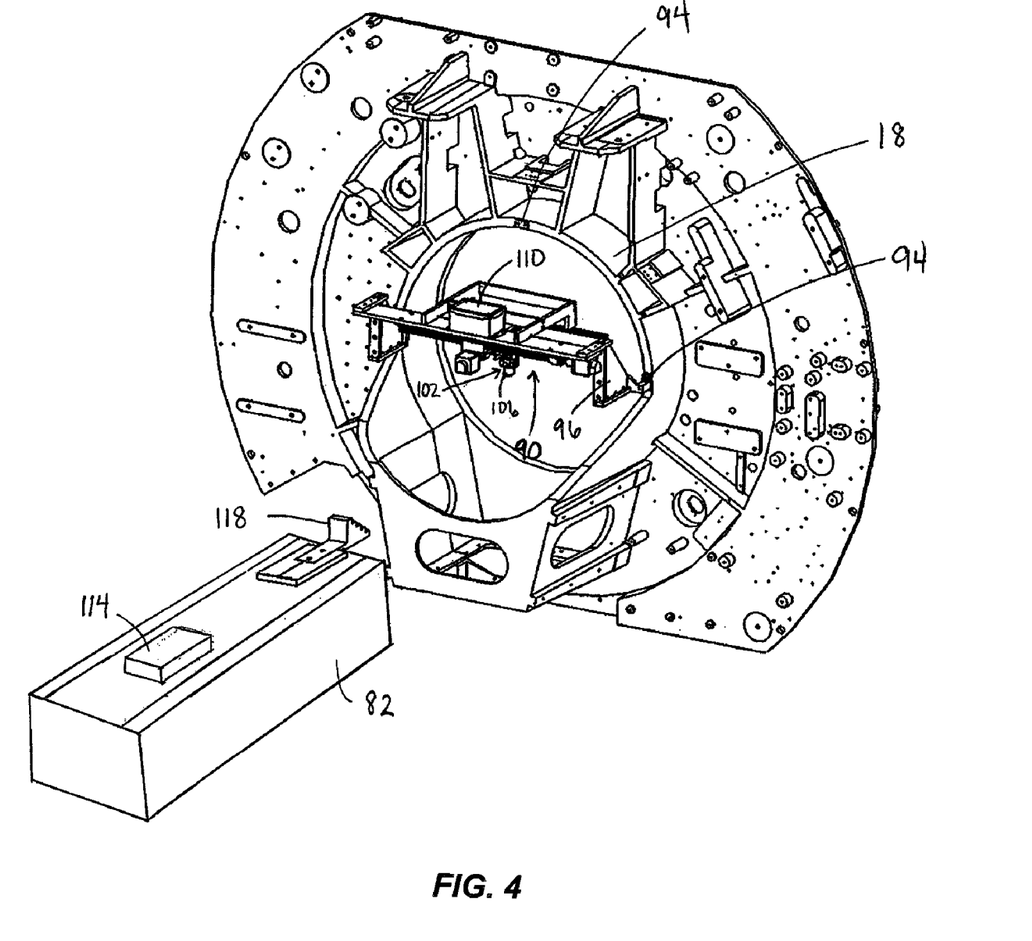
FIG. 4 is a perspective view of the twinning arm of FIG. 3 coupled to a gantry of the system of FIG. 1.

To accomplish the twinning process, additional hardware and/or software is coupled to the system 10. As illustrated in FIGS. 3 and 4, the system 10 includes a twinning arm 90. The arm 90 is coupled to the gantry 18 via a mounting pad 94 that is pre-mounted to the gantry 18. As shown in the illustrated embodiment, multiple mounting pads 94 are located about the gantry 18 to provide for multiple mounting locations. The mounting pads 94 are tightly toleranced so that the arm 90 can be mounted to the gantry 18 without the need for further tolerancing or adjustment. As shown, the arm 90 is bolted to the mounting pads 94 using a bracket 96. By coupling the arm 90 to the gantry 18, the control of the gantry and the arm 90 can be unified.

The arm 90 includes a two-dimensional (2D) scanner 98 that can take measurements in the x and y-directions. It is understood that in other embodiments, the arm 90 may include scanners capable of measuring in three dimensions, or in other numbers of dimensions. The twinning arm also includes an ion chamber 102 that receives signals from the linac 26. The ion chamber 102 includes a build-up cap 106 coupled thereto. In the illustrated embodiment, the build-up cap 106 is composed of virtual water and functions to increase the signal received in the ion chamber 102. Movement of the scanner 98 and the ion chamber 102 is accomplished using conventional controllers 110, 114. The height of the ion chamber 102 within the gantry aperture 32 is determined by the location of the mounting pads 94 and is adjusted using the isocenter of the gantry 18. In the illustrated embodiment, the height of the ion chamber 102 is not centered on the isocenter of the gantry 18, but rather the isocenter is used as a reference point to set the height of the ion chamber 102. In the illustrated embodiment, the ion chamber 102 is centered just above the isocenter of the gantry 18.

It should be understood that while a single ion chamber 102 is utilized in the illustrated embodiment, in other embodiments of the invention one or more ion chambers can be mounted in an array, grid, or volume. Utilizing multiple ion chambers would allow for more efficient calibration of a multi-dimensional radiation beam. It is further understood that while the illustrated embodiment utilizes an ion chamber as a detector, that other types of detectors, including but not limited to diode detectors, diamond detectors, etc., could be used in place of the ion chamber and still accomplish the desired results.

The system 10 also includes an attenuating block 118 that further assists with the twinning process. Conventional commissioning processes utilize a water tank to attenuate the signal from the linac to the ion chamber to make absolute measurements of dose, with the measurement device being submerged in the water tank. The depth of the water in the tank results in a known attenuation that can be used to adjust the components of the system. However, the use of the water tank in commissioning an individual system is unwieldy and difficult to adjust, as the water tank is often very large and difficult to move accurately into the path of the radiation beam. Further, with certain, more narrow beam geometries, it is difficult to get accurate measurements using the water tank. Additionally, any presence of water that could come in contact with the sensitive components of the system 10 adds additional uncertainty and risk. Thus, the system 10 utilizes the attenuating block 118, with the arm 90 coupled to the gantry 18 (i.e., without being submerged in water) to achieve the same results.

Figure 5A:
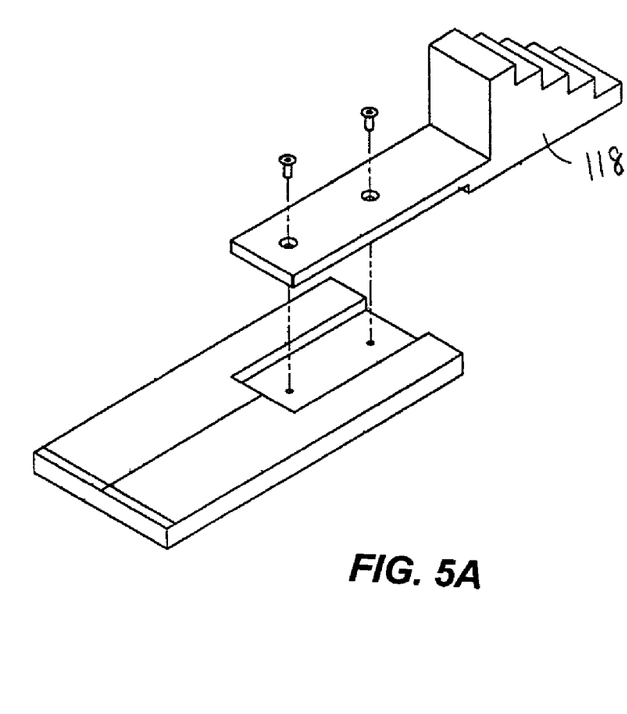
FIGS. 5A and 5B illustrate a perspective view and a side view, respectively, of an attenuation block coupled to the system of FIG. 1.
Figure 5B:
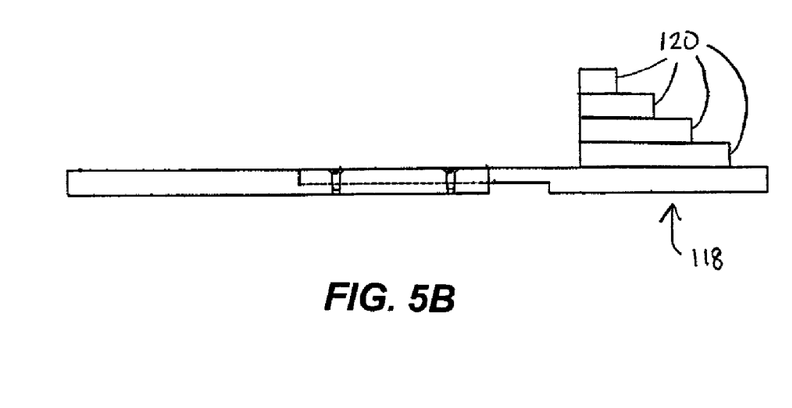
Figure 10:
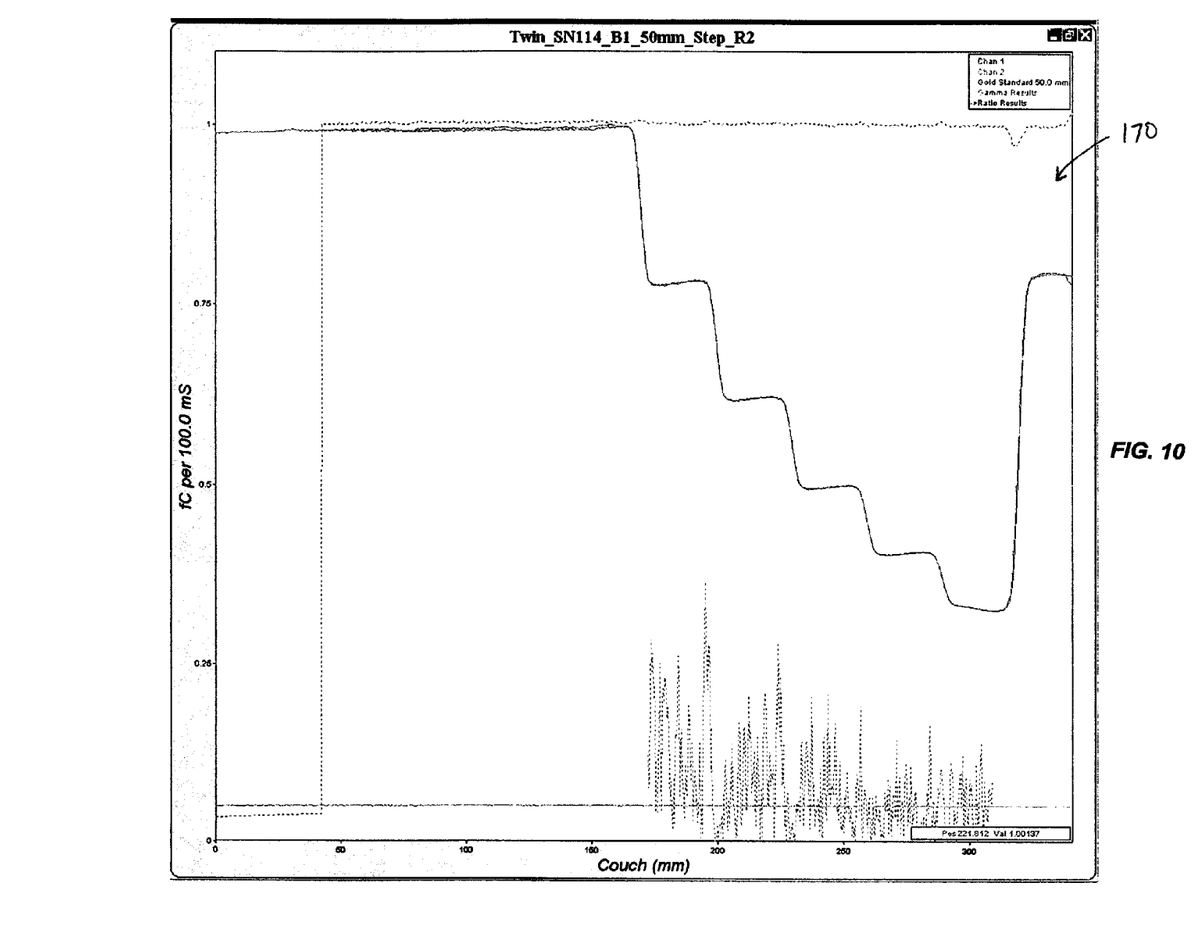
FIG. 10 is a graphical representation of data generated by the software of the invention illustrating the stepwise attenuation block data.

The attenuating block 118, as illustrated in FIG. 5, is substantially wedge-shaped and is formed of a stack of aluminum plates 120 of consistent thickness, resulting in a stepwise attenuation pattern (see FIG. 10 for a graphical representation of the stepwise attenuation pattern). The attenuating block 118 of the illustrated embodiment is coupled to the couch 82 and is moved into and out of the path of the radiation beam with movement of the couch 82 (i.e., the attenuating block 118 is moved into and out of the path of the x-ray source, which is the linac 26 in the illustrated embodiment). In other embodiments, the attenuating block 118 can be coupled to a separate device used to move the block 118 into and out of the path of the radiation beam generated by the linac 26. In further other embodiments, the attenuating block 118 may be stationary. The attenuation block 118 can be used for measurement with a beam having any given energy, though the thicknesses of the aluminum plates 120 (or the overall thickness of the attenuating block 118) may need to be adjusted to compensate for the beam strength.

The attenuating block 118 achieves similar attenuation results as the conventional use of the water tank. The results obtained by using the block 118 can be compared to the expected results from using the water tank attenuation. The use of aluminum as the material to form the attenuating block 118 has certain benefits. First, aluminum is denser than water such that less material is required to simulate a given depth of water. This reduces both the weight of the attenuator and the thickness of the required aluminum plates. Further, at the energy levels that are tested during the commissioning, service, and QA processes, the aluminum exhibits relatively similar properties to the water, making it easier to compare the attenuation results of the block 118 and the expected water results. However, any number of materials can be used to create the block so long as the signature of the material is known. For example, plastics or other metals can be used to create the block 118, though in many cases thicker plates of the other materials would be required to generate the same results as the aluminum plates. In addition, although the aluminum plates of the illustrated embodiment are all of equal thicknesses, in other embodiments the plates themselves can be of varied thicknesses, depending on the desired results.

Figure 6:
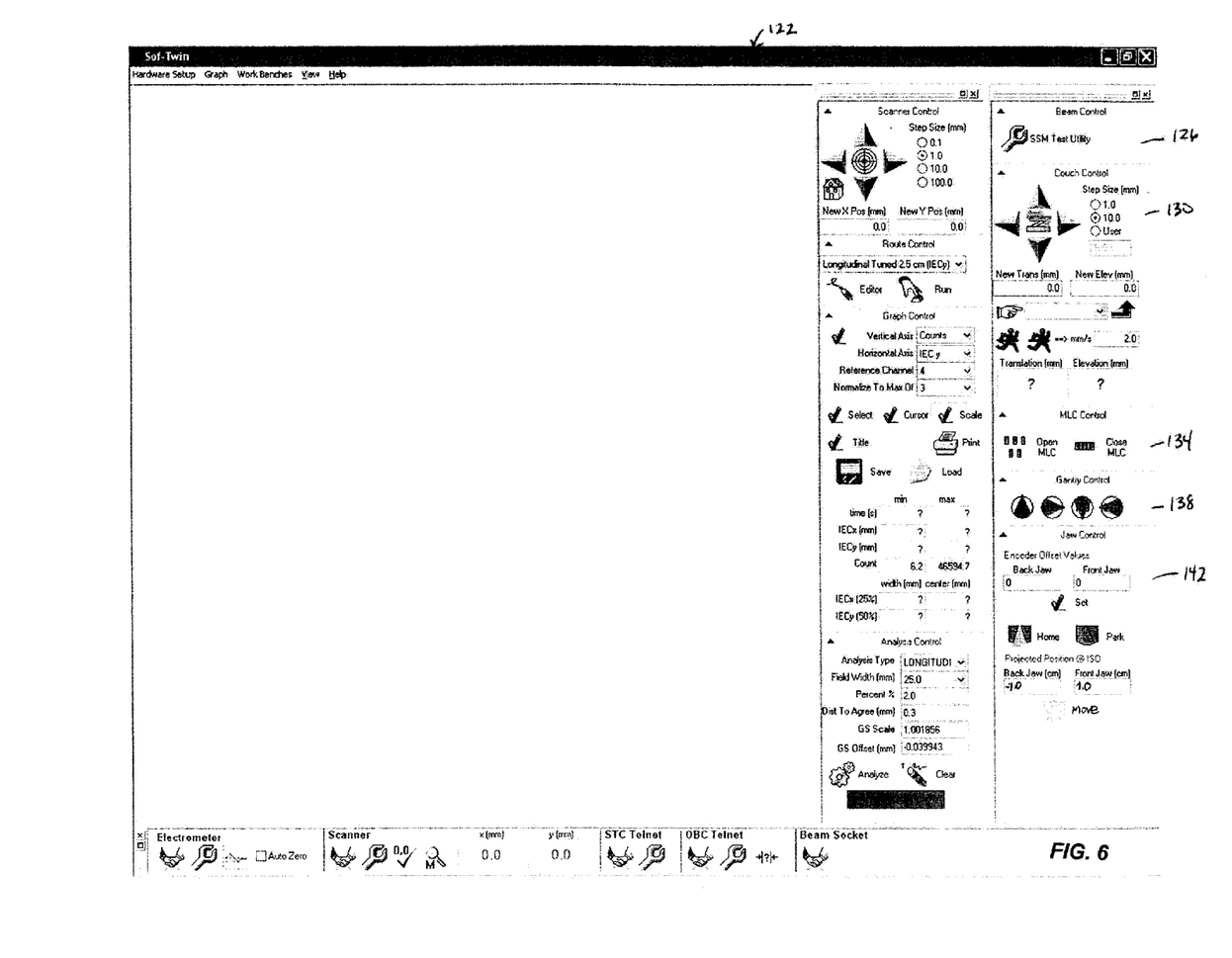
FIG. 6 is a screen shot of a representative user interface generated by software according to the invention.
Figure 7:
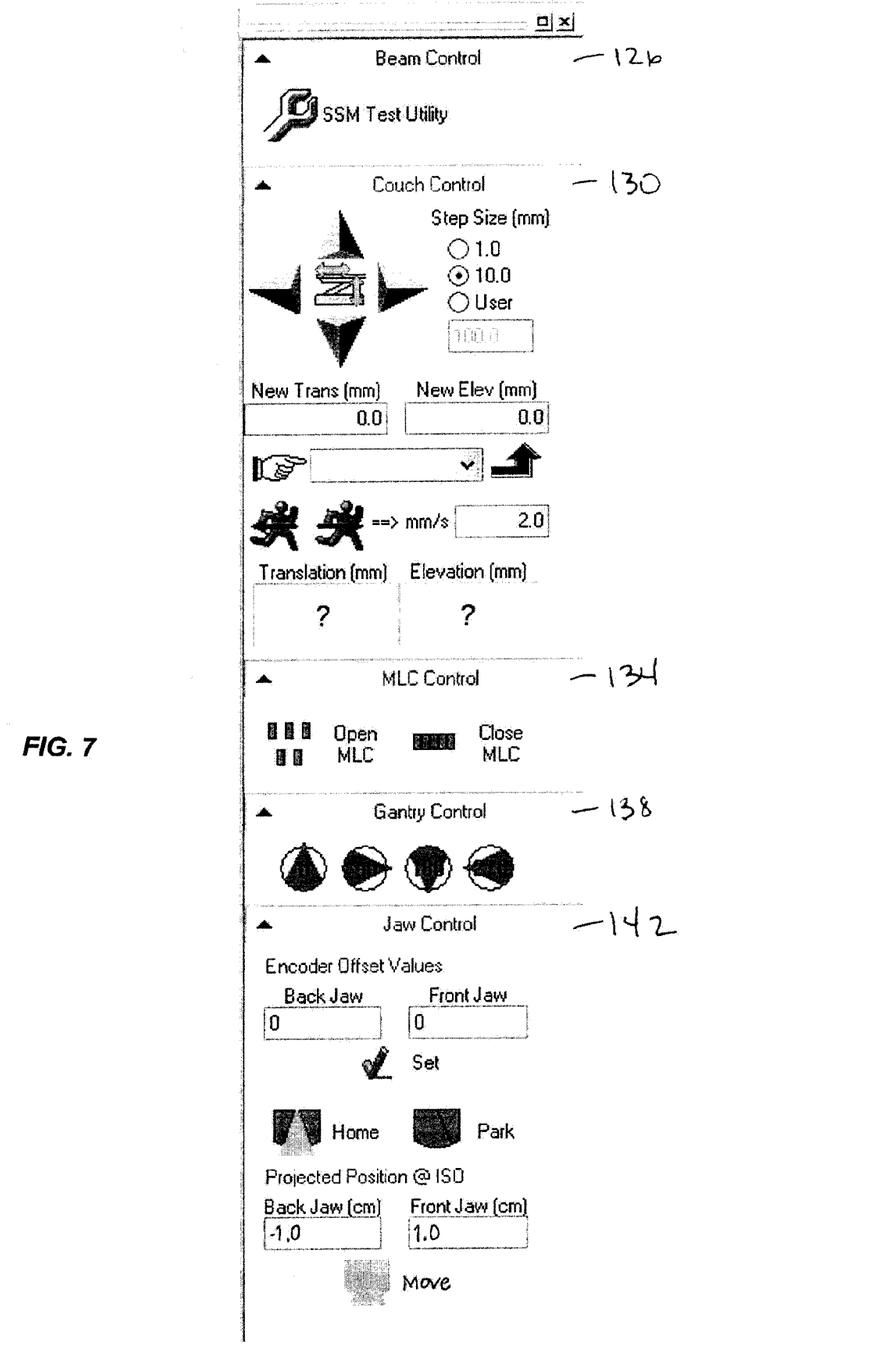
FIG. 7 is a screen shot of a portion of the user interface of FIG. 6, illustrating the component input features.

FIG. 6 illustrates a screen shot 122 generated on a graphical user interface of the system 10 by the software that controls the twinning process. As illustrated in FIGS. 6 and 7, the user can input information regarding the control of various portions of the system 10, including the beam (at 126), the couch 82 (at 130), the MLC 62 (at 134), the gantry 18 (at 138), and the jaws 46 (at 142). The software collects data from the system 10 and generates outputs, such as the graphical representations illustrated in FIGS. 8-10. The software provides for efficient system tuning by integrating the control and measurement functions, and is essentially fully automated. The software includes fixed scripts that determine how to appropriately collect the data generated by the system 10. Thus, if any of the measurements gathered by the software are found to be outside of the predetermined range, the software itself can determine how to appropriately change the inputs to generate the desired results. The software can have a feedback mechanism to take the data, remediate the data where necessary, and then re-measure the data without requiring further input from the user.

Figure 8:
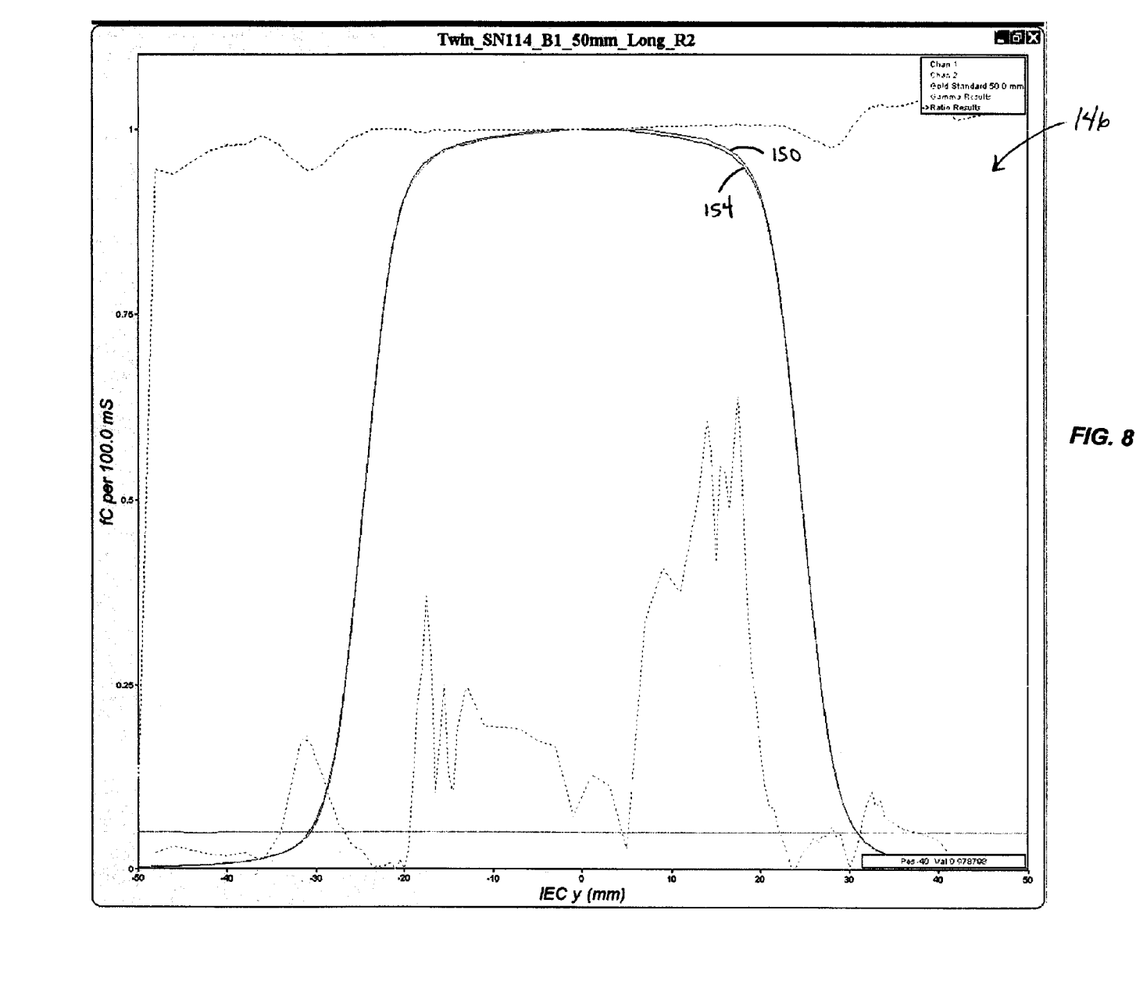
FIG. 8 is a graphical representation of data generated by the software of the invention illustrating the longitudinal profile data.
Figure 9:
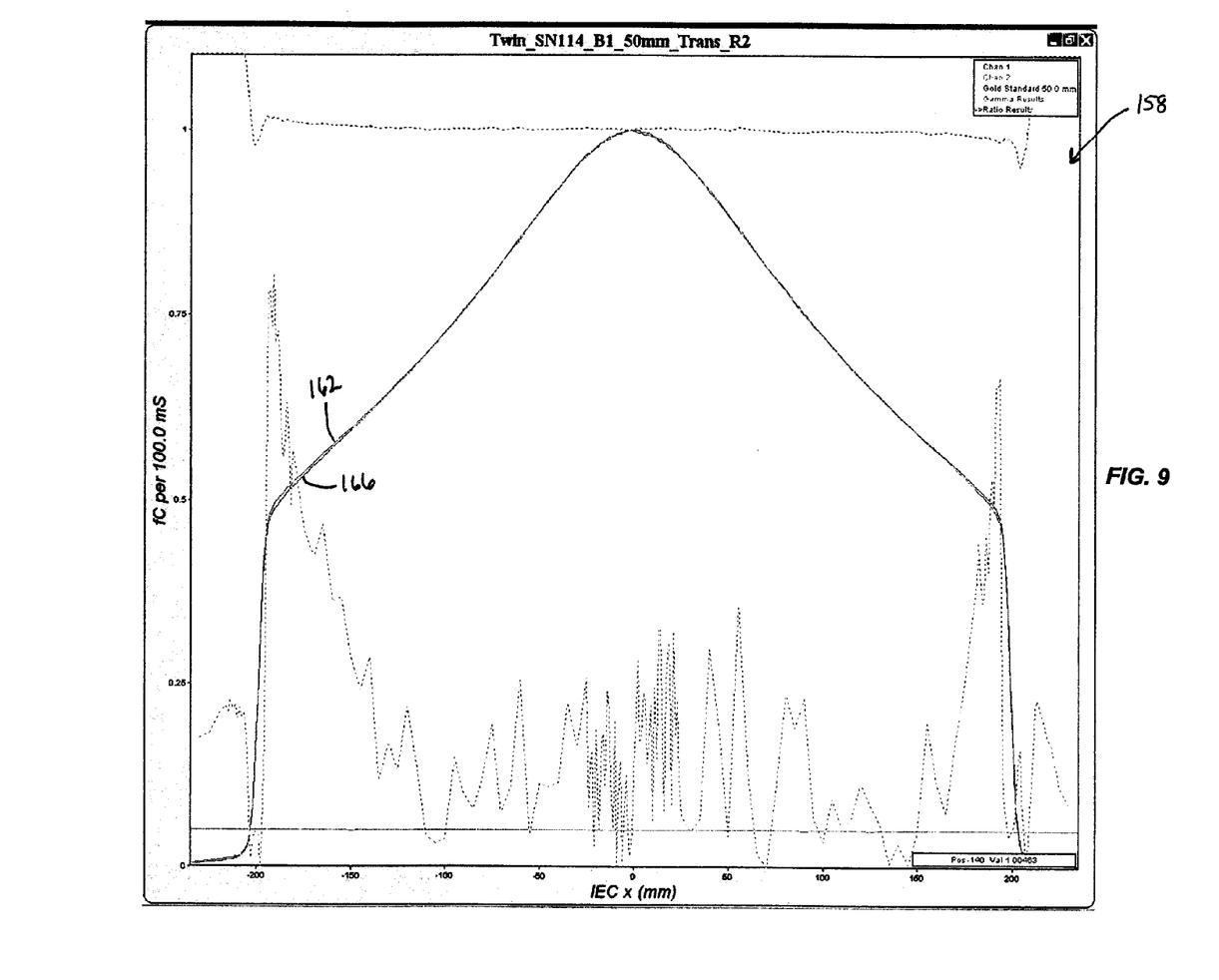
FIG. 9 is a graphical representation of data generated by the software of the invention illustrating the transverse profile data.

FIG. 8 is an exemplary graphical output created by the software. The graph 146 represents the longitudinal profile (i.e., the IEC y-direction data) of the beam. The shape of the graph 146 is determined by the position of the jaws 46. The graph 146 includes a first data line 150 (shown in purple) generated from data received by the ion chamber 102 overlaid onto the gold standard data line 154 (shown in gray) for a twinned system 10. As illustrated, the first data line 150 is virtually identical to the gold standard data line 154, confirming that the system 10 is twinned to the gold standard in the y-direction. Similarly, FIG. 9 is a graph 158 representing the transverse profile data (i.e., the x-direction data) of the beam. Here again, a first data line 162 (in purple) is overlaid onto the gold standard data line 166 (in gray) to confirm the twinning in the x-direction. Both the longitudinal and transverse profile data are a function of the shape of the beam 30. FIG. 10 is a graphical output 170 representing the attenuation data of the step-wedge attenuation block 118.

Figure 11:
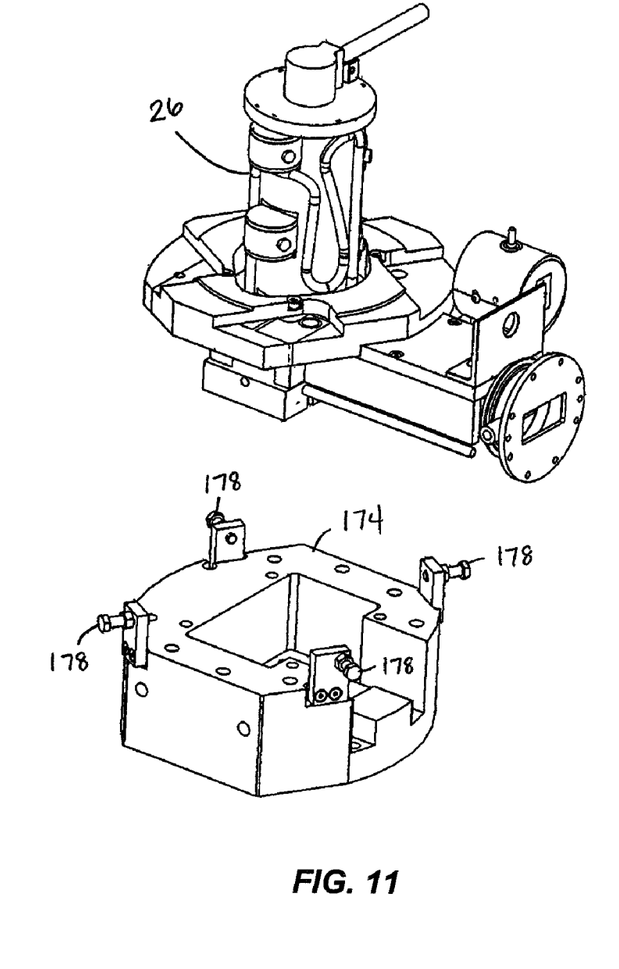
FIG. 11 is an exploded view of a linac mounting bracket according to one embodiment of the invention.
Figure 12:
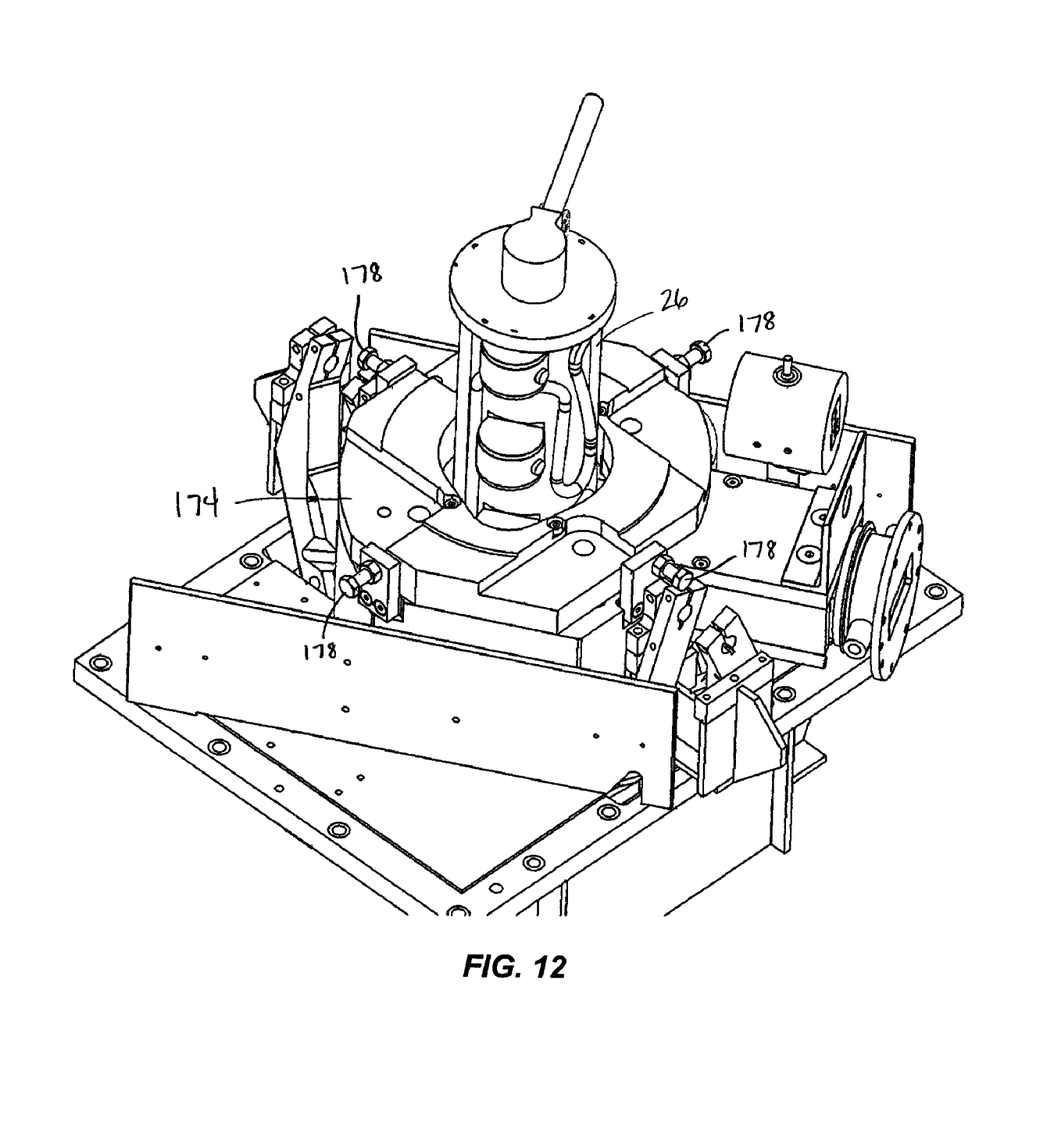
FIG. 12 is an assembly view of the linac mounting bracket illustrated in FIG. 11.

FIG. 11 illustrates an adjustment bracket 174 according to an embodiment of the invention. The adjustment bracket 174 includes a plurality of fasteners, shown as bolts 178, which allow for easy adjustment of the linac 26 on the gantry 18. During the alignment phase of the twinning process, the linac 26 needs to be aligned, or "dialed-in", so to speak. In previously known linac mounting configurations, the linac did not move naturally in the x-direction independently of motion in the y-direction, and vice versa. The natural motion was closer to diagonal in effect. Thus, it was difficult to accurately move the linac and any movement made had a compound effect, with an x-direction component and a y-direction component. By moving the opposing sets of bolts 178, the bracket 174 allows for independent movement of the linac 26 in the x and y-directions so that the linac 26 can be adjusted with precision and with ease.

In the embodiments described above, certain components, such as the arm 90 and the attenuating block 118, have been described for use together in commissioning, servicing, or performing QA on the system 10. However, it is understood that in other embodiments of the invention, certain components can be used separately, or can be used to perform other functions within the system 10.

For example, it is understood that as the gantry 18 rotates, the arm 90, and thus the ion chamber 102, will rotate with the gantry 18. By rotating the arm 90, other measurements are possible, such as measurements of the changes in beam field shape, the measurement of any gantry sag, etc. In some gantry configurations, such as with C-arm gantries, it is important to ensure that the beam is consistent at all angles. The beam geometry can be validated using the arm 90 (e.g., the scanner 98) without using the attenuation block 118. If preferred, a separate movement apparatus can be utilized to move the block 118 into the path of the linac 26 at any beam angle. Other measurement functions, such as measuring energy output of the linac 26, can also be performed without the use of the block 118.

In other embodiments, where the system includes a detector opposite the x-ray source, the arm 90 can be used to gather calibration data in both the x and y-directions. This allows for more robust calibration of the detector, as the data could be used to determine how the detector signals vary with system wobble. The calibration would thus be a function of gantry angle, rotation, and stability. The arm 90 could be replaced with a detector or detector array operable to measure in two dimensions (e.g., measure the y-profile in addition to the x-profile).

When multiple ion chambers (or multiple detectors) are utilized to measure for different beam penetration depths, there would be no need for a separate attenuation block. In essence, in some embodiments, the attenuation block and ion chambers could be integrated into one unit.

The data generated by the system 10 utilizing the twinning mechanisms described above can also be used in various other ways. For example, in other embodiments the arm 90 and/or block 118 can be used to get profiles for single leaves 66 of the MLC 62. The leaves could be static or moving and characterizing the output during leaf motion. The MLC could be the MLC 62 illustrated above, or could be a two-dimensional MLC having sliding leaves. We could also calibrate for all jaw thicknesses, altering the beam shape to get different field shapes in the y-direction. In yet other embodiments, especially those where the linac is designed to be movable, the arm 90 and/or block 118 can be used to get beam characteristics as a function of the position of the linac, or vice versa. Thus, the device could be used for linac tuning. The apparatus could also be used in an MLC tongue and groove test for MLC alignment. In some cases, the arm 90 could be normalized out of the measurement, where appropriate.

Overall, the use of the twinning mechanisms discussed above make the commissioning, servicing, and QA analyses of the system 10 much simpler as very little set-up is required. The time to commission an individual system drops from a few days to a few hours. Additionally, measuring any system against the gold standard, rather than individually commissioning the machine, cuts down on training and servicing time, and allows for greater patient mobility between machines to receive treatment. All beam field sizes can be easily commissioned using these processes, as the twinning process described above can create a generic calibration that will yield a commissioning for any arbitrary field size. Adjustment after service and re-tuning of the system as needed during the life of the machine are also much more efficient, and service issues are easier to diagnose on twinned systems.

We claim:

1. A radiation therapy treatment system comprising:
   a gantry;
   a radiation source coupled to the gantry and operable to produce a beam of radiation; and
   a measurement device physically connected to the gantry, the measurement device including
   a multi-dimensional scanning arm, and
   a detector operable to receive radiation from the radiation source.

2. The radiation therapy treatment system of claim 1, further comprising an attenuation block coupled to the system.

3. The radiation therapy treatment system of claim 2, wherein the attenuation block is movable.

4. The radiation therapy treatment system of claim 3, wherein the attenuation block is movable into and out of the path of the radiation beam produced by the radiation source.

5. The radiation therapy treatment system of claim 2, wherein the attenuation block is not comprised of water.

6. The radiation therapy treatment system of claim 2, wherein the attenuation block is substantially step-shaped.

7. The radiation therapy treatment system of claim 2, wherein the attenuation block comprises a plurality of plates coupled together to form a wedge.

8. The radiation therapy treatment system of claim 7, wherein the plates are of substantially uniform thickness.

9. The radiation therapy treatment system of claim 7, wherein the thickness of each plate is variable to adjust for beam strength.

10. The radiation therapy treatment system of claim 2, wherein the attenuation block is formed of aluminum.

11. The radiation therapy treatment system of claim 2, wherein the attenuation block is formed of plastic.

12. The radiation therapy treatment system of claim 1, wherein the scanning arm moves in any combination of the x, y, and z directions.

13. The radiation therapy treatment system of claim 1, wherein the detector is an ion chamber.

14. The radiation therapy treatment system of claim 13, wherein the detector includes multiple ion chambers.

15. The radiation therapy treatment system of claim 14, wherein the ion chambers are arranged in one of a grid, an array, or a volume.

16. The radiation therapy treatment system of claim 1, wherein the detector includes one of a diode detector or a diamond detector.

17. The radiation therapy treatment system of claim 16, wherein the detector includes a plurality of detectors.

18. The radiation therapy treatment system of claim 17, wherein the plurality of detectors are arranged in one of a grid, an array, or a volume.

19. The radiation therapy treatment system of claim 1, further comprising an adjustment bracket coupled to the radiation source, and wherein the adjustment bracket is operable to adjust the position of the radiation source in both first and second directions, and wherein the movement of the radiation source in each of the first and second directions is independent of the movement in the other of the first and second directions.

20. The radiation therapy treatment system of claim 1, wherein the measurement device includes a plurality of detectors.

21. The radiation therapy treatment system of claim 1, wherein the system has a unified control system for the scanning arm and the gantry.

22. The radiation therapy treatment system of claim 1, wherein the scanning arm is not in contact with water.

23. A method of commissioning a radiation system to a previously defined standard, the radiation system including a measurement device coupled to a gantry and a radiation source capable of producing radiation, the method comprising:
   generating radiation from the radiation source;
   passing the radiation through an attenuation block;
   positioning the measurement device such that it is not in contact with water;
   receiving radiation with the measurement device;
   generating data from the radiation received; and
   commissioning the system using the generated data to match system characteristics to the previously defined standard.

24. The method of claim 23, wherein commissioning the system using the generated data includes comparing the generated data to the previously defined standard.

25. The method of claim 24, wherein commissioning the system further comprises consideration of one or more of the following: alignment, beam output, beam energy, beam shape, beam symmetry, output fluence rate, wavelength of energy emitted, penetration depth of the radiation, and field width.

26. The method of claim 23, wherein the system includes a collimator located in the path of radiation produced by the radiation source, and wherein generating data from the radiation received includes one of characterizing collimator output, calibrating for multiple field shapes, measuring beam characteristics as a function of the position of the radiation source, and aligning the collimator.

27. The method of claim 23, further comprising moving the attenuation block into and out of the path of the radiation.

28. The method of claim 23, wherein receiving the radiation with the measurement device further comprises receiving the radiation using a detector, and wherein the detector includes an ion chamber.

29. The method of claim 23, further comprising moving the radiation source independently in first and second directions, the movement allowing for adjustment of the position of the radiation source.

30. The method of claim 23, wherein commissioning the system to match system characteristics to the previously defined standard includes matching characteristics to a previously defined standard that is based upon measurements in a water tank.

31. The method of claim 23 wherein the measurement device is independently-calibrated to a known standard.

32. The method of claim 23 wherein the measurement device is an ion chamber.

33. The method of claim 32 wherein the ion chamber is configured to measure electric charge of the radiation received from the radiation source after at least a portion of the radiation passes through the attenuation block.

34. The method of claim 32 wherein the ion chamber is independently-calibrated to a known standard.

35. The method of claim 23 wherein the measurement device is removably coupled to the gantry.

36. The method of claim 23 wherein the measurement device is removably coupled to the gantry and wherein the measurement device moveable to a second radiation system to be commissioned.

37. A method of tuning a radiation therapy system to meet a predefined standard of operating parameters, the radiation therapy system utilizing system controls, the method comprising:
- passing radiation through an attenuation block;
- collecting data utilizing a measurement device, the data relating to system outputs;
- comparing the data to the predefined standard of operating parameters;
- providing feedback to the system based on the comparison; and
- adjusting the system controls using the feedback so that the system outputs meet the predefined standards.

38. The method of claim 37, wherein the adjustment is automatic.

39. The method of claim 37, wherein the adjustment is manual.

40. The method of claim 37, wherein the radiation therapy system further comprises an attenuation block, and wherein collecting data utilizing the measurement device includes collecting data utilizing a measurement device physically separated from the attenuation block.

* * * * *